（12）United States Patent
Nomoto et al.

(10) Patent No.: US 7,215,807 B2
(45) Date of Patent: *May 8, 2007

(54) NONDESTRUCTIVE INSPECTION METHOD AND APPARATUS

(75) Inventors: Mineo Nomoto, Yokohama (JP); Daiske Katsuta, Yokohama (JP); Toshio Asano, Hiroshima (JP); Kaoru Sakai, Yokohama (JP); Tetsuo Taguchi, Hitachi (JP); Isao Tanaka, Tokai (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/190,220

(22) Filed: Jul. 26, 2005

(65) Prior Publication Data

US 2005/0259861 A1  Nov. 24, 2005

Related U.S. Application Data

(63) Continuation of application No. 09/698,810, filed on Oct. 26, 2000, now Pat. No. 6,950,545.

(30) Foreign Application Priority Data

Oct. 26, 1999  (JP) .................................. 11-303480

(51) Int. Cl.
 *G06K 9/00* (2006.01)
(52) U.S. Cl. ................ 382/141; 356/237.2; 356/239.8; 356/243.4; 356/369; 382/165; 382/170

(58) Field of Classification Search ............. 356/237.1, 356/237.2, 239.8, 243.4, 369; 382/141, 146, 382/165, 152, 170
See application file for complete search history.

(56) References Cited

U.S. PATENT DOCUMENTS

| 5,835,220 | A | * | 11/1998 | Kazama et al. | ............ | 356/369 |
| 6,434,257 | B1 | * | 8/2002 | Mohan et al. | ............ | 382/110 |
| 6,618,079 | B1 | * | 9/2003 | Higuchi | .................. | 348/223.1 |
| 6,950,545 | B1 | * | 9/2005 | Nomoto et al. | ............ | 382/141 |
| 6,975,391 | B1 | * | 12/2005 | Asano et al. | ............ | 356/237.1 |
| 2005/0259861 | A1 | * | 11/2005 | Nomoto et al. | ............ | 382/141 |

\* cited by examiner

*Primary Examiner*—Gregory Desire
(74) *Attorney, Agent, or Firm*—Townsend and Townsend and Crew LLP

(57) ABSTRACT

The present invention relates to a method for inspecting a crack in a metal surface or the like, and, particularly, to an inspection method and apparatus for nondestructive inspection such as liquid penetrant inspection and magnetic particle testing. The present invention provides a flaw inspection method that essentially comprises the steps of illuminating a surface of a sample to be inspected, obtaining an image of the surface, characterizing a potential flaw on the inspected surface by processing the obtained image, displaying an image of the potential flaw, verifying that the potential flaw is a true flaw, and storing an image of the verified flaw in memory.

10 Claims, 17 Drawing Sheets (a)

(b)

(a)

Chromaticity image (b)

(c)

Color hue image (a)

Chromaticity image (b)

(c)

Color difference image (a)

(b)

NONDESTRUCTIVE INSPECTION METHOD AND APPARATUS

CROSS-REFERENCES TO RELATED APPLICATIONS

The present application is a continuation application which claims priority to U.S. application Ser. No. 09/698,810, filed Oct. 26, 2000 now U.S. Pat. No. 6,950,545 and claims priority from Japanese Patent Application Reference No. 11-303480, filed Oct. 26, 1999.

BACKGROUND OF THE INVENTION

The present invention relates to a method for inspecting a crack in a metal surface or the like, and particularly, to an inspection method and apparatus for nondestructive inspection such as liquid penetrant inspection and magnetic particle testing.

Liquid penetrant inspection and magnetic particle testing are nondestructive inspection methods for inspecting a flaw such as a fracture (crack) in a metal surface. In the liquid penetrant inspection, a red liquid ("penetrant") is typically applied to an inspected surface. The penetrant is wiped off after a predetermined period, and a white powder ("developer") is applied to the surface. If there is a flaw such as a crack, the developer draws the penetrant remaining in the crack to the surface, revealing the location, shape and size of the flaw.

In magnetic particle testing, a solution that includes fluorescent magnetic powder is applied to a magnetic object under inspection; then the object is magnetized. If there is a flaw such as a crack, the magnetic flux concentrates on the flaw, attracting the fluorescent magnetic powder. Under ultraviolet light, the magnetic powder emits green light which outlines any flaw. Conventionally, verification of these flaw indicators has been only by visual observation.

In the case of conventional inspection by visual observation, a flaw may be overlooked because of an inspector's fatigue, or the inspection results may differ due to differences of perception or opinion among individual inspectors. Further, the inspection result is recorded merely as a word, "passed" or the like. Thus, there is a problem in reliability of inspection.

Moreover, in magnetic particle testing, an automatic inspection apparatus has been developed for use with important and mass-produced parts; however, the apparatus is specialized, and various shaped parts cannot be readily inspected.

Further, in liquid penetrant inspection surface colors must be detected as a highly precise two-dimensional distribution. Even if a colorimeter capable of high precision chromaticity measurement is used, two-dimensional sweeping is necessary. Thus, it is difficult from the standpoint of inspection time and cost to automatically inspect various shaped parts.

In addition, when an object under inspection is large, it may be difficult to distinguish the part of the object corresponding to an image obtained by automatic inspection, or to discern the part of the object corresponding to a detected flaw.

Further, the economical value will be dramatically improved if both of the liquid penetrant inspection and the magnetic particle testing could be performed automatically by one apparatus.

SUMMARY OF THE INVENTION

An object of the present invention is to provide a flaw inspection method, a flaw inspection apparatus, and a flaw inspection assisting method that solve the above-described problems and facilitate determination of true flaws.

Another object of the present invention is to provide a flaw inspection method, a flaw inspection apparatus and a flaw inspection assisting method that readily discerns the location of a flaw, even in a large object under inspection.

In an embodiment of the present invention, to attain the above objects, a color video camera is used to perform image pickup on an object under inspection. Note that if an unmodified color video camera is used in liquid penetrant inspection, image pickup cannot be properly performed because of reflected light from the illuminated object. Further, in magnetic particle testing, all the foreign materials and the like on the object under inspection emit light due to illumination by ultraviolet light, making differentiation between these materials and the flaws difficult. Accordingly, a polarizing filter is provided in both luminaire and camera. Further, in a specific embodiment of the present invention, to remove the reflection of light, and, to reduce the ultraviolet light, a filter is provided in front of the camera.

Further, in the embodiment of the present invention, since the color camera, a white light and an ultraviolet light are provided in one probe, the probe can be used in both liquid penetrant inspection and magnetic particle testing. In liquid penetrant inspection, the xy chromaticity of the surface of the object under inspection is calculated from a video signal from the color video camera, to detect a red flaw indication. In magnetic particle testing, differentiation processing is performed on a green video signal so as to enhance and detect a flaw.

Further, to prevent oversight and over-detection in automatic inspection, in one embodiment of the present invention the inspection result is displayed as a color image, and a portion judged as a flaw in the automatic inspection is surrounded by a rectangle so that an inspector can check each rectangular portion in an original image to determine whether it is a true flaw. The original image and the inspection result are stored as a record in a magneto-optic disk or the like.

Further, in one embodiment of the present invention, if the object under inspection is, e.g., long and cannot be seen within the viewing screen, a scale is provided in an image pickup viewing screen, and image pickup is simultaneously performed on the scale and an inspection image to specify the inspection position.

Further, in the embodiment of the present invention, in the method based on liquid penetrant inspection, color calibration of the color video camera employs conversion parameters for xyY values unique to the color video camera, which are generated by using signals obtained by image pickup with the color video camera for R (red), G (green), B (blue) and W (white) reference colors. An image obtained by image pickup on the surface of the inspected object is temporarily converted with the conversion parameters, and a potential flaw is detected by using the converted image.

These and other objects, features and advantages of the embodiments of the present invention will be apparent from the following detailed description of the preferred embodiments of the invention, as illustrated in the accompanying drawings.

BRIEF DESCRIPTION OF THE DRAWINGS

In FIG. 3(a) a filter is not attached.

In FIG. 4(a) a filter is not attached.

FIG. 9(b) is an x chromaticity value of the largest number of pixels; and FIG. 9(c) is a y chromaticity value of the largest number of pixels.

FIG. 10(b) is an xy chromaticity plane, or chromaticity diagram; and FIG. 10(c) is a diagram indicating hue at position (i,j) of an image.

FIG. 16(b) is a luminance distribution on line 161 in FIG. 16(a); FIG. 16(c) is an image of a flaw; and FIG. 16(d) indicates a judgment threshold value 164 in a differentiation diagram.

FIG. 22(a) is an example of image pick up ranges on an inspection surface; FIG. 22(b) is complete image information for each object; and FIG. 22(c) illustrates divided images of the object.

DESCRIPTION OF THE SPECIFIC EMBODIMENTS

Hereinafter, an example of the present invention will be described with reference to the drawings.

Figure 1:
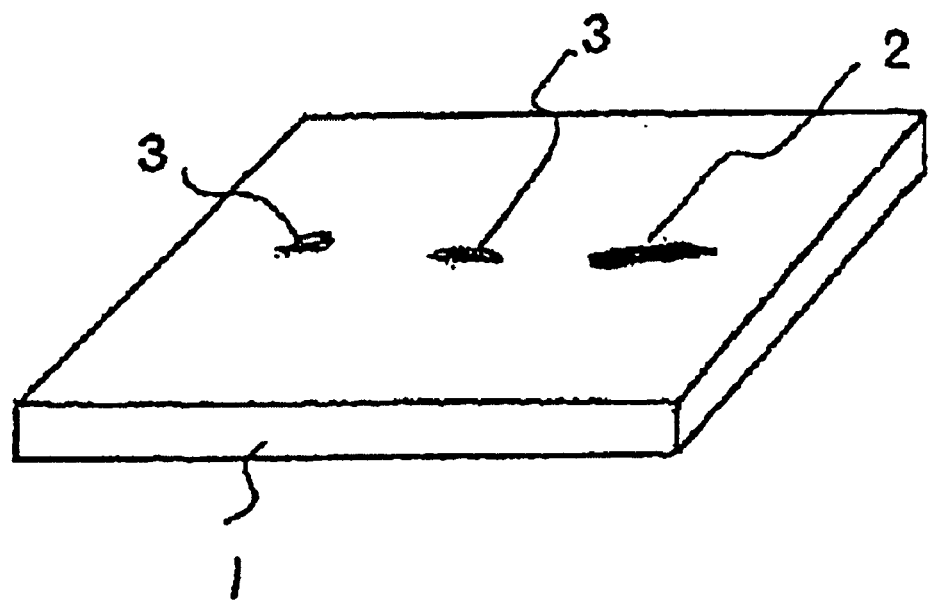
FIG. 1(a) is a perspective view showing an example of an object under liquid penetrant inspection according to one embodiment of the present invention.
FIG. 1(b) is a perspective view showing an example of an object under magnetic particle testing according to one embodiment of the present invention.
Figure 1:
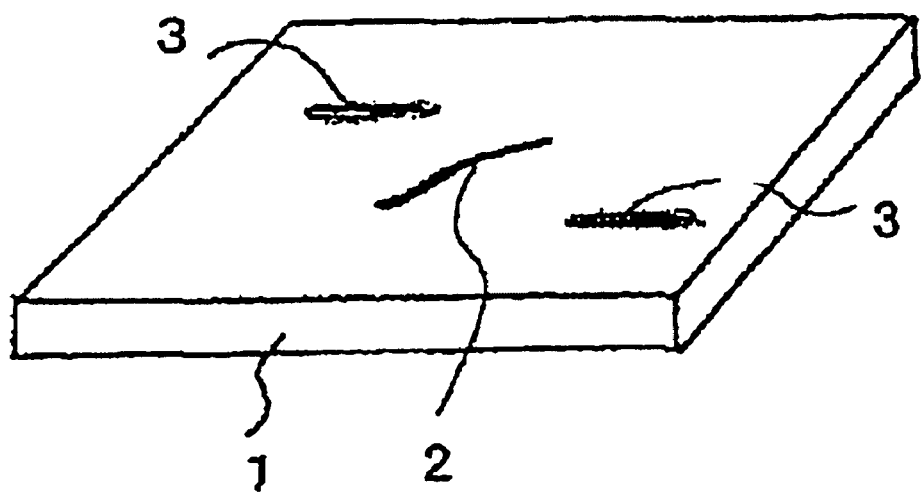

FIGS. 1(a) and (b) show an example of a flaw to be inspected in accordance with the present invention.

FIG. 1(a) shows an example of liquid penetrant inspection. An object under inspection 1 (hereinafter "object 1") is coated with white development liquid, and a flaw 2 (contrast: high) and a pseudo flaw 3 (contrast: low) are observed. In the liquid penetrant inspection, flaw 2 is enhanced and displayed as a red indication mark. The pseudo flaw appears as a pale red indication mark, such as when the penetrant has remained in a surface grinding streak or the like and has not been completely polished out.

FIG. 1(b) shows an example of magnetic particle testing. Fluorescent magnetic powder has been applied to object 1 having flaw 2, and the object has been magnetized. When the object is illuminated with ultraviolet light, the fluorescent magnetic powder collected at flaw 2 emits green light. However, if object 1 has, e.g., a welded portion, as the fluorescent magnetic powder collects along the bead, the pseudo flaw 3 may appear in green.

Figure 2:
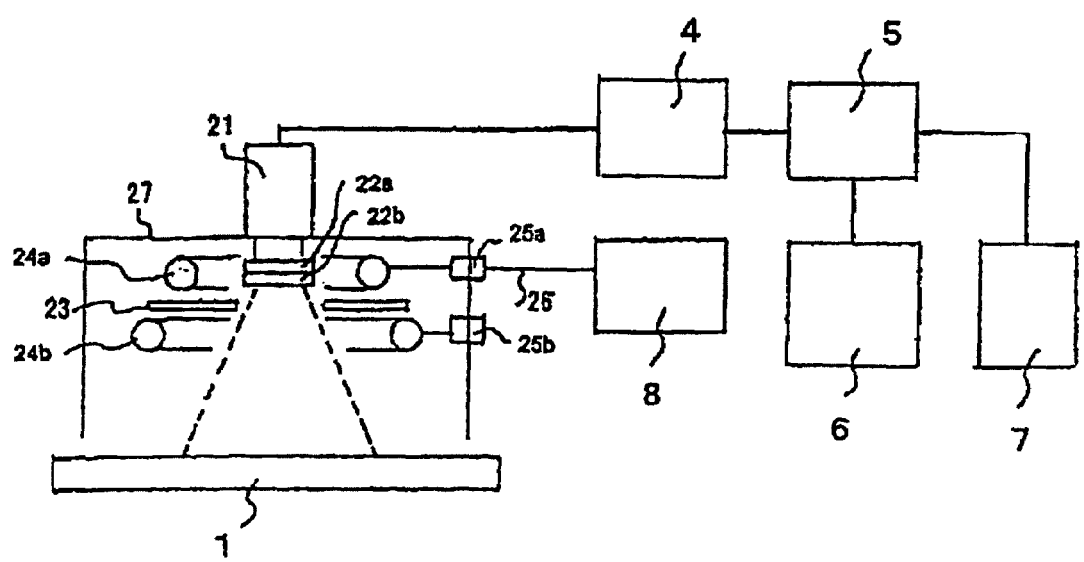
FIG. 2 is a front view of the schematic construction of the flaw inspection apparatus showing one working example according to an embodiment of the present invention.

FIG. 2 is a block diagram showing the construction of a flaw inspection apparatus according to the present invention. Object 1 has flaw 2 and pseudo flaw 3. Image pickup is performed on the object using a color video camera 21. In liquid penetrant inspection, a white light 24a is used for illumination, while in magnetic particle testing, an ultraviolet light 24b is used for illumination. The white light 24a is connected to a white light connector 25a, and to an illumination power source 8 via an illumination cable 26.

In magnetic particle testing, illumination cable 26 is connected to an ultraviolet illumination connector 25b. To avoid influence by extraneous light, a hood 27 is attached to the light. In FIG. 2, the light is a ring-shaped light, however, one or more bar-shaped lights may be employed.

A color video signal from the color video camera 21 includes independent R, G and B signals, or the signal may be a composite video signal. In any case, the video signal is stored as R, G and B image data in a color image memory 4. The color image data is analyzed by a computer 5, and the result of flaw detection is displayed on a color monitor 6. Computer 5 has a memory for storing a program and data, a processor for processing data detected by the color video camera 21, and an input/output interface connected to a keyboard (not shown) and to a color monitor 6.

The flaw inspection result is stored in a data storage device 7. Further, the image displayed on color monitor 6 can be printed out, as needed.

A polarizing filter 22a and an ultraviolet-light reduction filter 22b are attached to the front side of the lens of color video camera 21. Further, a polarizing filter plate 23 is provided below white light 24a. Polarizing filter 22a and the polarizing filter plate 23 are used to prevent projection of white light and reflection from object 1 during liquid penetrant inspection. Polarizing filter 22a is rotated while an output video signal from the color video camera 21 is monitored, and the polarizing filter is fixed at a position where the projection of illumination light and reflection are most effectively prevented. Polarizing filter 22a may be automatically adjusted based on the video output signal from the color video camera 21.

The ultraviolet light reduction filter is used for preventing unnecessary light emission from foreign materials and the like attached to object 1 when ultraviolet light 24b is used during magnetic particle testing.

Figure 3:
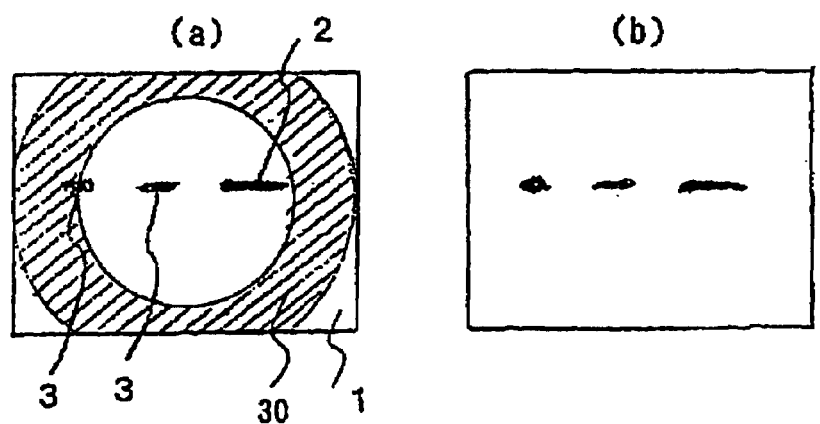
FIGS. 3(a) and (b) are front views of the monitor display screen showing the effect of a polarizing filter.
in FIG. 3(b) a filter is attached.

FIG. 3 illustrates the effects of the polarizing filter 22a and the polarizing filter plate 23.

FIG. 3(a) shows a display on the monitor screen when the filters are not used; and FIG. 3(b), a display on the monitor screen when the filters are attached and the rotational angle of the filter is adjusted. In FIG. 3(a), projection of light 30 impedes flaw detection. The light is projected in a ring shape since white illumination light 24a is a ring type light. In FIG. 3(b), the projection does not occur.

Figure 4:
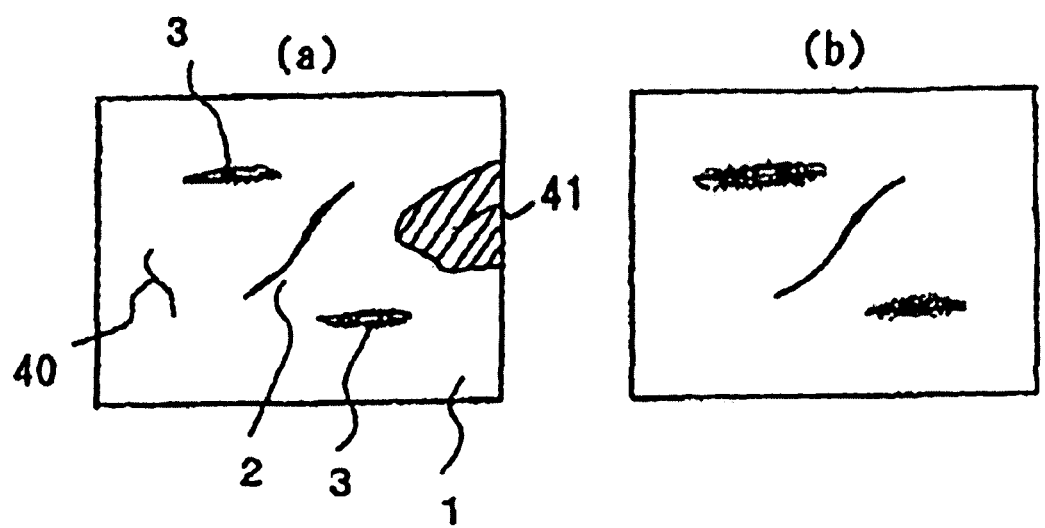
FIGS. 4(a) and (b) are front views of the monitor display screen showing the effect of the ultraviolet light reduction filter.
in FIG. 4(b) a filter is attached.

FIGS. 4(a) and (b) illustrate the effect of the ultraviolet light reduction filter 22b. FIG. 4 (a) shows a display on the monitor screen when the filter is not used; and FIG. 4(b), a display on the monitor screen when the filter is attached. In FIG. 4(a), light emission from a foreign material 40, such as lint, and positive reflection 41 from object 1, obtained by image pickup with color video camera 21, impede flaw inspection. In FIG. 4(b), these noises are reduced, and the image shows light emission only from the fluorescent magnetic powder as in the case of visual observation of the product under inspection 1 by a human inspector.

Figure 5:
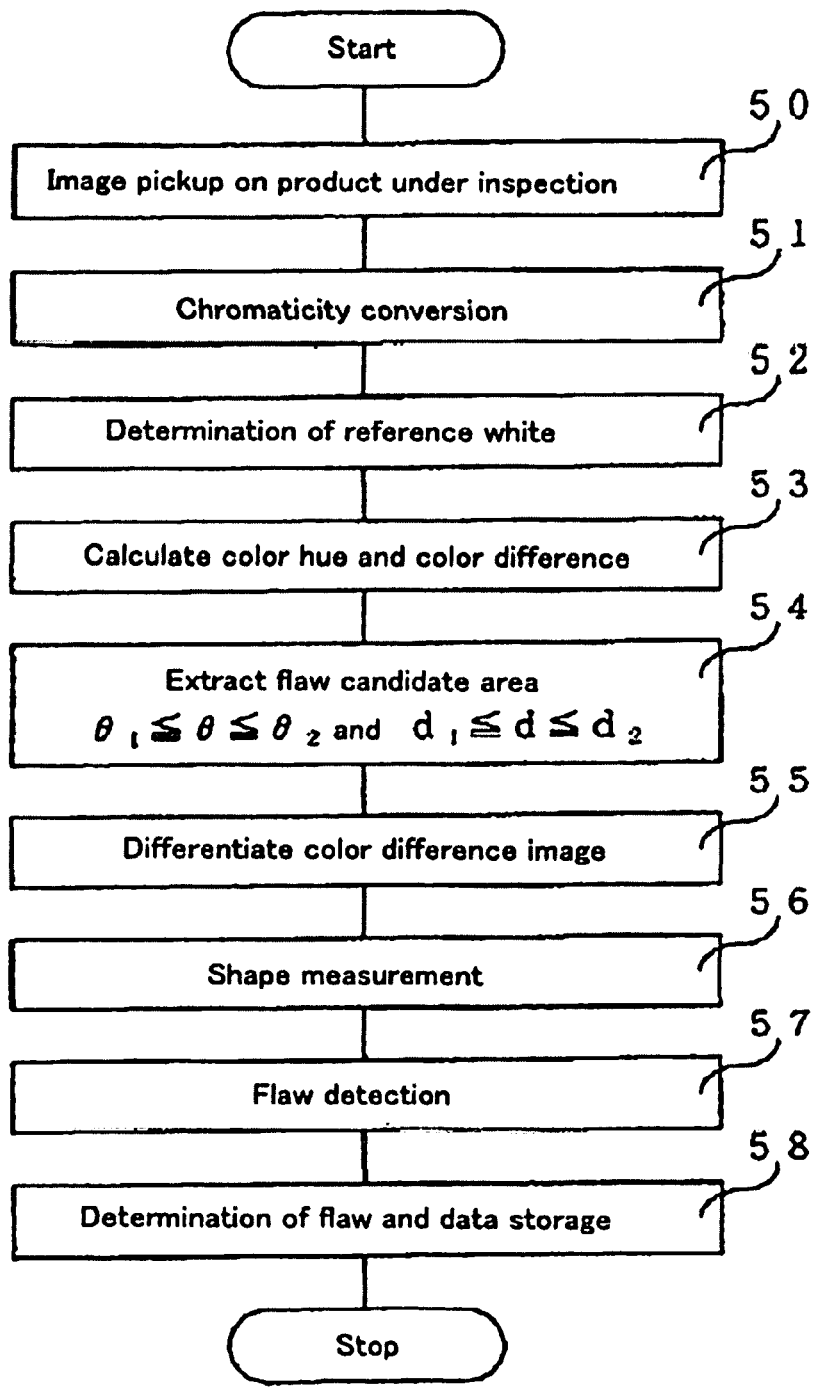
FIG. 5 is a flowchart showing the flow of the automatic inspection method in a liquid penetrant inspection according to an embodiment of the present invention.

The method of crack flaw detection in a liquid penetrant inspection image will now be described with reference to FIGS. 5 to 15. FIG. 5 shows an automatic detection method for flaw 2 in the liquid penetrant inspection.

First, image pickup 50 is performed, using white light 24a, on object 1, which is coated with developer. Next, chromaticity conversion 51 is performed to obtain xy chromaticity values of the respective pixels from the R, G and B color image data.

Next, determination of reference white 52 is performed to calculate the reference white chromaticity of the developer, and calculation of color hue and color difference 53 is performed in each position of the image with respect to the reference white.

Thereafter, to extract flaw candidate area 54, the area of color hue and color difference within a specific range is extracted by binarization.

In most cases a true flaw 2 has a clear outline, and a pseudo flaw has an unclear outline. Accordingly, differentiation of color difference image 55 is performed to obtain the change rate for the color difference in the outline portion of the extracted flaw candidate area. Next, shape measurement 56 is performed to measure the area, the ratio of length to width, and the length of the flaw candidate area. Thereafter, flaw detection 57 is performed to detect only an area having a high color difference change rate, and a length and area equal to or greater than the predetermined values for true flaw 2. Further, the inspection result is displayed on color monitor 6 for the inspector's flaw verification; then image data, shape data, positional information and the like are stored in storage device 7, or printed out and stored as a hard copy (58).

Figure 6:
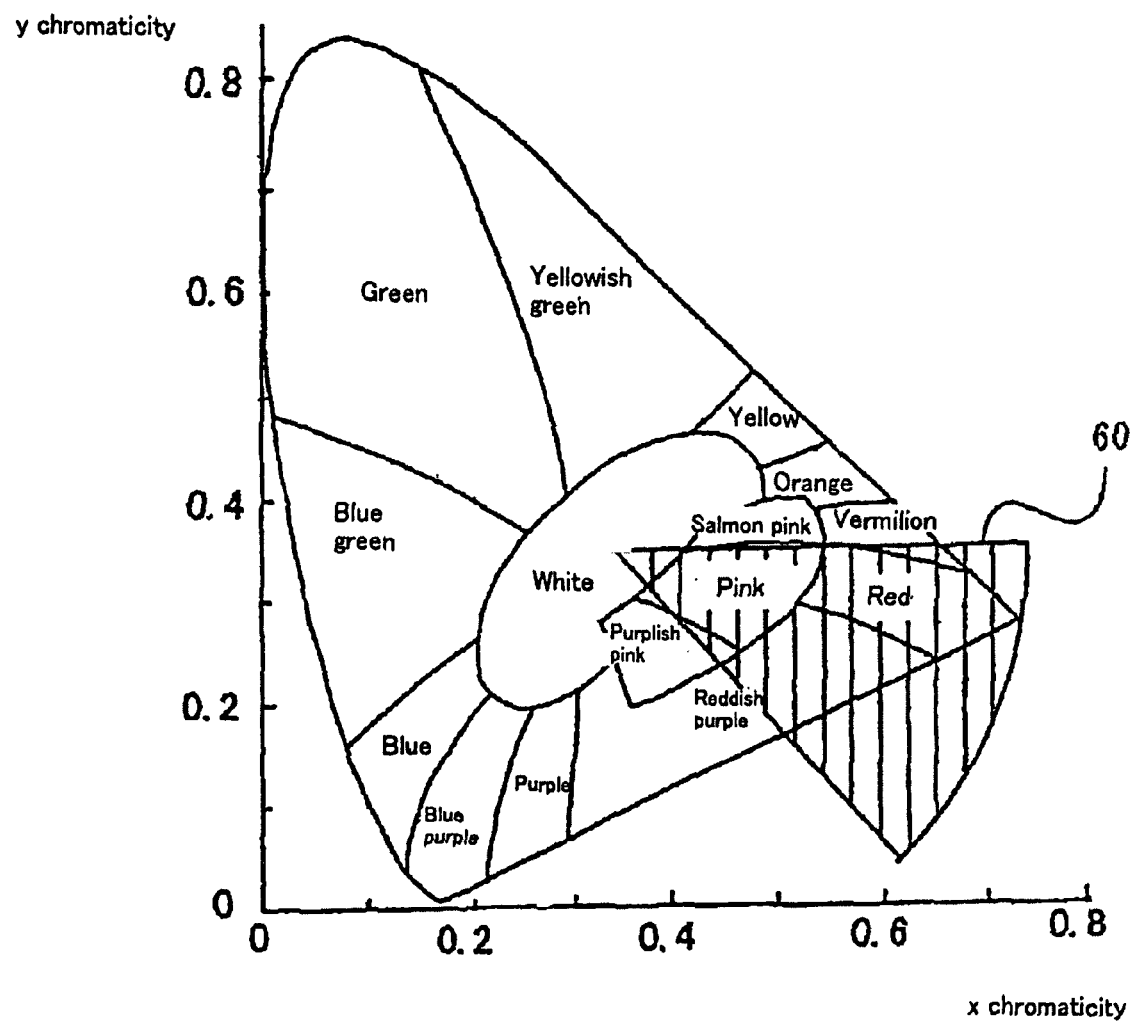
FIG. 6 is an xy chromaticity diagram.

Inspection by color requires quantitative color evaluation. Accordingly, at chromaticity conversion step 51, the RGB data of the obtained color image is converted to chromaticity x, y, and luminance Y defined by the CIE (Commission Internationale de l'Eclairage), and inspection is performed using the data. The two-dimensional orthogonal coordinate representation of the chromaticity x, y, as shown in FIG. 6 is called a chromaticity diagram. In the chromaticity diagram, colors are arranged around a white center, and the respective colors become more vivid as they get farther away from white. Hereinafter, a color tone will be called a color hue, and vividness of respective colors, saturation, and a distance between two chromaticity values on the chromaticity diagram, a color difference. FIG. 6 shows a color difference range 60 for a liquid penetrant inspection image.

Figure 7:
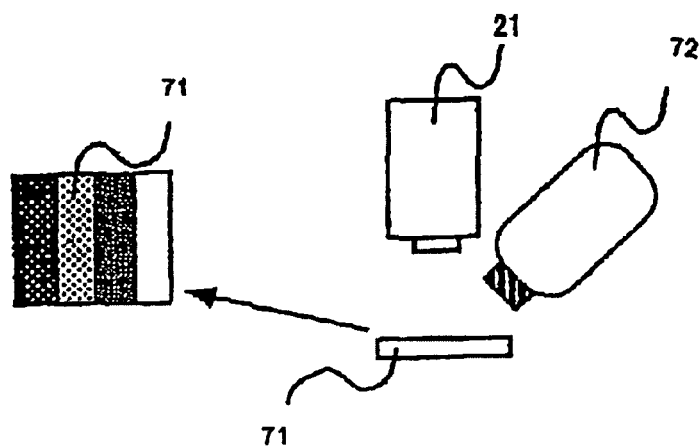
FIG. 7 is a front view of the construction for camera calibration.
Figure 8:
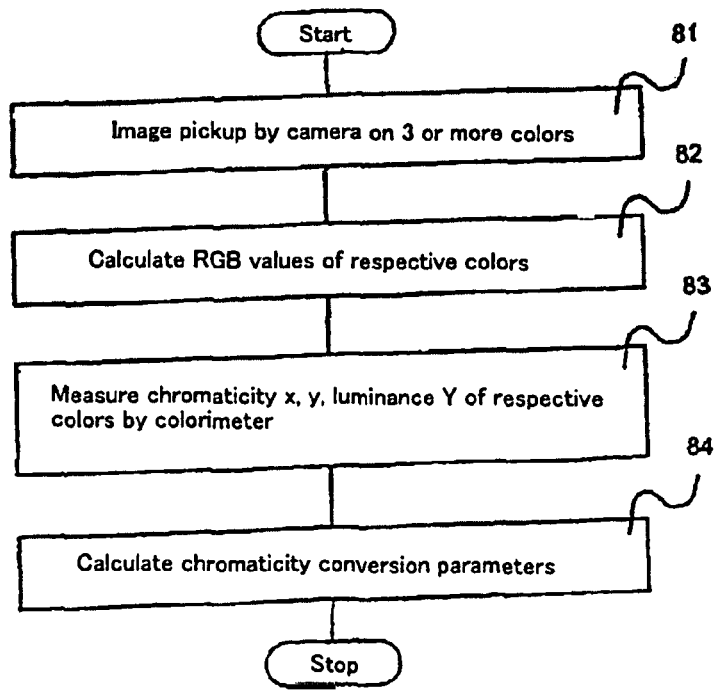
FIG. 8 is a flowchart showing the flow of camera calibration processing.
Figure 9:
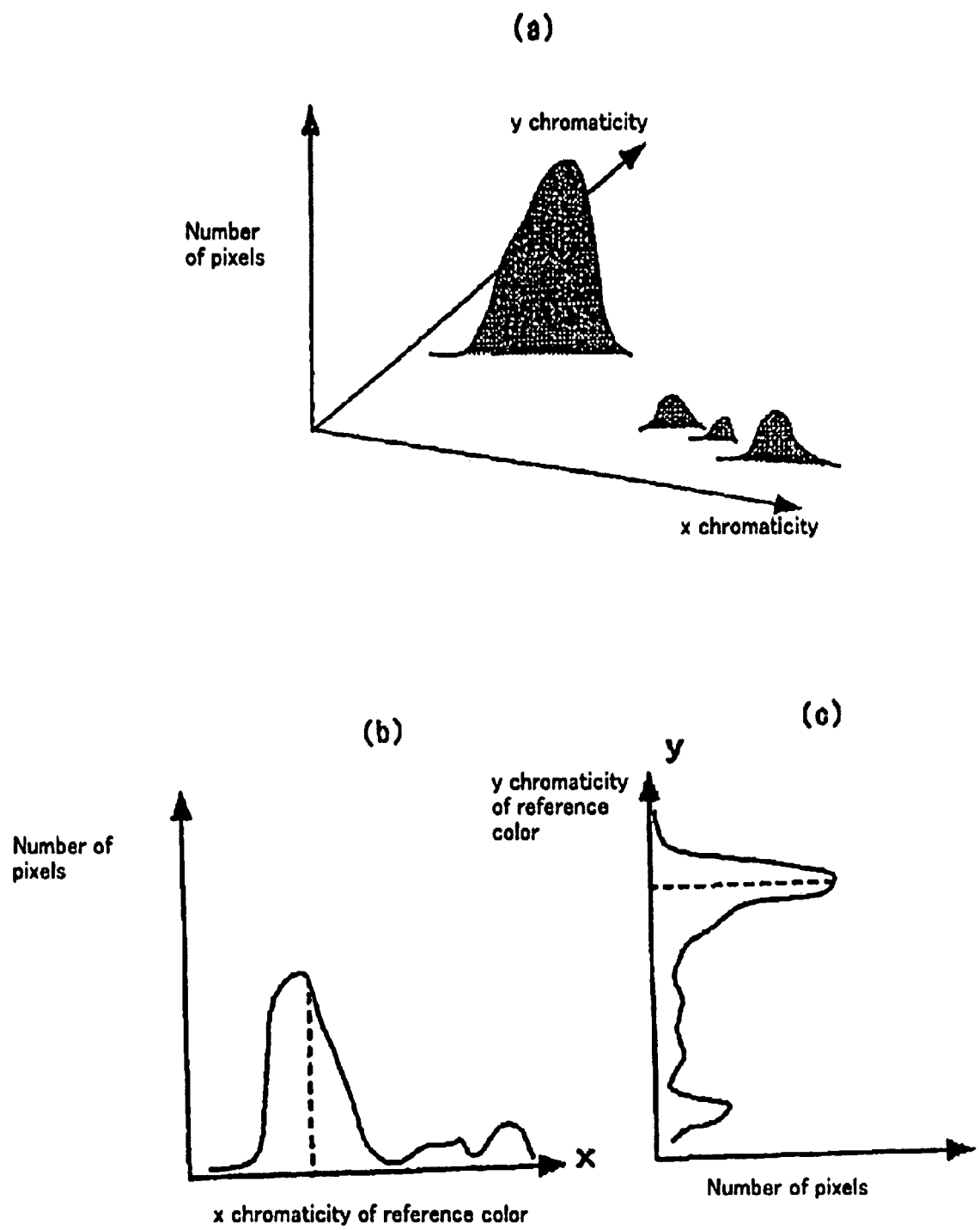
FIG. 9 (a) is a two-dimensional chromaticity histogram.

In a specific embodiment, to convert the RGB data to the chromaticity x, y and luminance Y with high precision, color calibration is performed in advance using a camera calibration color chart 71 as shown in FIG. 7. FIG. 8 shows the flow of the processing. Camera calibration color chart 71 is coated with three or more colors. It is subjected to image pickup by color video camera 21 (81), to calculate RGB values of the respective colors (82). Further, the chromaticity x, y and luminance Y of these colors are measured by a colorimeter 72 (83). The relation between RGB values and the xyY values is represented by (Expression 1) and (Expression 2).

$$\begin{pmatrix} X \\ Y \\ Z \end{pmatrix} = \begin{pmatrix} a_{11} & a_{12} & a_{13} \\ a_{21} & a_{22} & a_{23} \\ a_{31} & a_{32} & a_{33} \end{pmatrix} \begin{pmatrix} R \\ G \\ B \end{pmatrix} \quad (j=1,2,3) \quad \text{(Expression 1)}$$

Note that X, Y and Z are called tristimulus values.

$$\text{Chromaticity } x = \frac{X}{X+Y+Z} \quad y = \frac{Y}{X+Y+Z} \quad \text{(Expression 2)}$$

$$\text{Luminance } Y$$

Accordingly, if the RGB values of the respective colors obtained from the camera are substituted into (Expression 1) and (Expression 2) to calculate the xyY values, and values $a_{11}$ to $a_{33}$ corresponding to the xyY values measured by the colorimeter are obtained, conversion parameters unique to the camera can be obtained. Since the number of unknown parameters is 9, the parameters can be calculated by at least three color RGB values $(R_1G_1B_1)$ to $(R_3G_3B_3)$ and corresponding xyY values of the colorimeter $(x_1y_1Y_1)$ to $(x_3y_3Y_3)$ From (Expression 2), XYZ can be calculated from the xyY values by the following (Expression 3), $$X=Yxx/y, \ Y=Y, \ Z=Yx(1-x-y)/y \quad \text{(Expression 3)}$$

The xyY values of the three colors from the colorimeter are substituted into (Expression 3), to obtain XYZ, and the XYZ are substituted into (Expression 1).

$$\begin{pmatrix} X_1 \\ Y_1 \\ Z_1 \end{pmatrix} = \begin{pmatrix} a_{11} & a_{12} & a_{13} \\ a_{21} & a_{22} & a_{23} \\ a_{31} & a_{32} & a_{33} \end{pmatrix} \begin{pmatrix} R_1 \\ G_1 \\ B_1 \end{pmatrix} \quad (j=1,2,3) \qquad \text{(Expression 4)}$$

By this expression, conversion parameters $a_{11}$ to $a_{33}$ unique to the camera are obtained 84, and the xyY values equal to those of the colorimeter can be obtained from the RGB values of the camera.

For the camera calibration color chart 71 used in the liquid penetrant inspection, the arrangement of R, G, B and W reference colors and plural types of colors ranging from the white of the developer to the red of the penetrant is preferable for color calibration. The reproducibility of conversion parameters can be checked by selecting a white which is close to that of the developer liquid, pink as the color of the flaw candidate, and red to correspond to a flaw, from a chromaticity range 60 of the liquid penetrant inspection image in FIG. 6, in a stepwise manner; and measuring the xyY values and comparing these values with respective xyY values calculated by using the previously generated conversion parameters for the xyY values unique to the camera. Reliable and high-precision chromaticity measurement can be easily realized by checking the color reproducibility periodically by using the color chips as shown in FIG. 6 in (or preferably prior to) liquid penetrant inspection.

Further, the present inventors have observed that the reference colors of the above color chart differ depending on the color temperature of the illumination light source. That is, in liquid penetrant inspection with the white illumination light used in the embodiment of FIG. 2 as the light source, and, in liquid penetrant inspection with a halogen lamp as the light source.

Since the chromaticity range in FIG. 6 may differ, the color calibration chromaticity must be selected in correspondence with the light source.

Further, the chromaticity from white to red differs depending on the difference of the color tone of the surface of object 1 (a smooth bright surface of a metal such as stainless steel, a leather-like dark surface of iron or the like, a rusty brown surface etc.). Accordingly, the conversion to xyY can be performed with higher precision by performing color calibration with increased numbers of interpolation colors in white, pink and red.

Further, it is preferable to select the chromaticity of the reference colors of red, green, blue, white, and colors changing from white to red, in correspondence with the chromaticity of the developer and the penetrant.

When the RGB values obtained from the camera are chromaticity-converted to xyY values using the conversion parameters unique to the camera, as calculated by prior calibration, and the chromaticity distribution in the image is calculated, at step 52, calculation is performed using the chromaticity of the developer, i.e., the chromaticity of portions other than a flaw, as a reference value. First, the chromaticity values x, y of each pixel in the image are examined, and the number of pixels of each x, y value is counted; thus, a two-dimensional chromaticity histogram is generated as the graph of FIG. 9(a).

Then, the x chromaticity value of the largest number of pixels (FIG. 9(b)) and the y chromaticity value of the largest number of pixels (FIG. 9(c)) in the image are obtained. As most of the image portions include no flaw, the x, y chromaticity values of the peak value in the two-dimensional chromaticity distribution are the x, y chromaticity values of the reference white.

Figure 10:
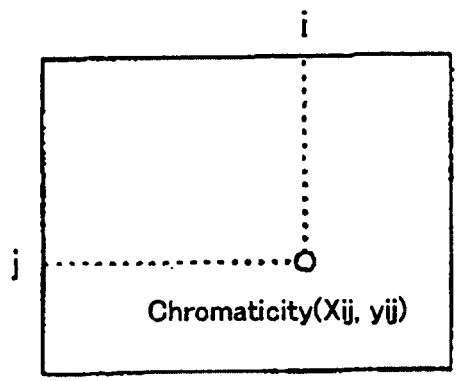
FIG. 10 (a) is a diagram indicating chromaticity at position (i,j) of an image.
Figure 10:
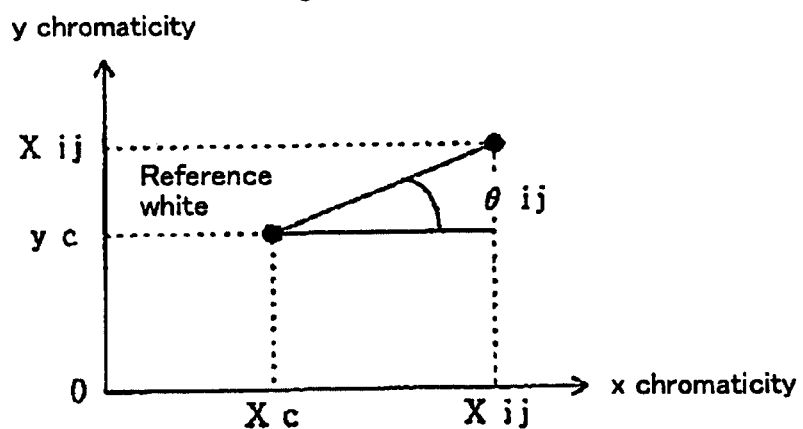
Figure 10:
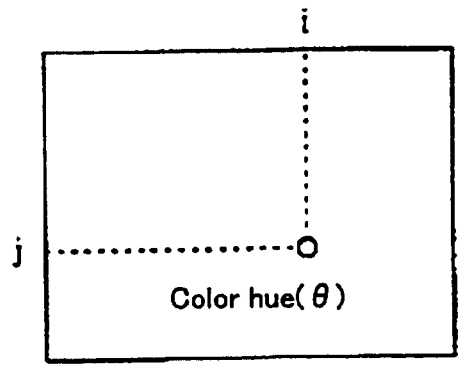

At step 53, the color hue and color difference in each position on the image with respect to the reference white are calculated. Assuming that the chromaticity of the reference white is $(x_c, y_c)$, and the chromaticity in a position in the image is $x_{ij}, y_{ij}$, the color hue in a position (i, j) is calculated in a direction toward the reference color on the chromaticity diagram as shown in FIG. 10. The calculation expression is as represented by (Expression 5).

$$\text{Color hue: } \theta_{ij} = \tan^{-1}\left(\frac{y_{ij}-y_c}{x_{ij}-x_c}\right) \qquad \text{(Expression 5)}$$

Figure 11:
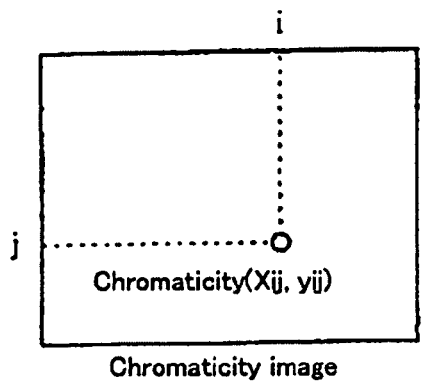
FIG. 11(a) is a diagram indicating chromaticity at position (i,j) of an image.
FIG. 11(b) is an xy chromaticity plane, or chromaticity diagram, indicating a color difference.
FIG. 11(c) is a diagram indicating hue at position (i,j) of an image.
Figure 11:
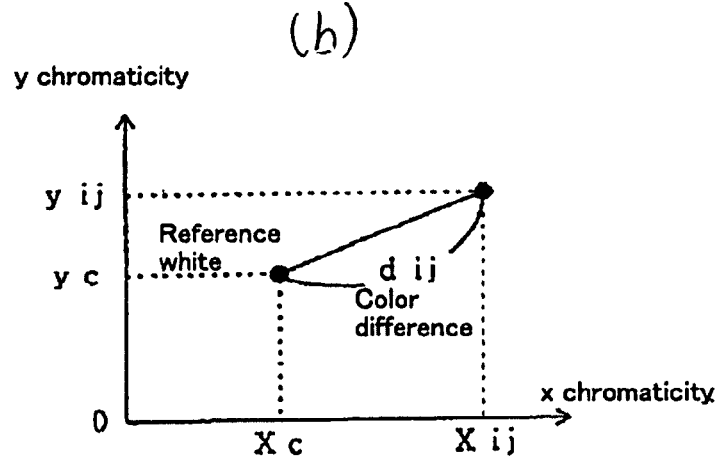
Figure 11:
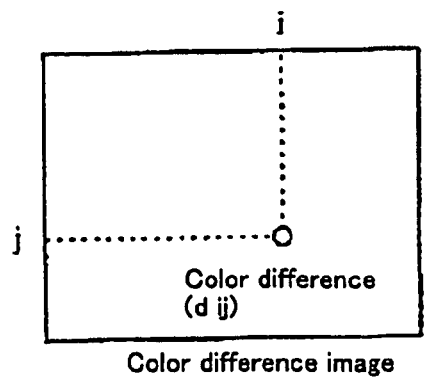

Further, as shown in FIG. 11, the color difference in the position (i, j) is calculated with a distance from the reference color on the chromaticity diagram. The calculation expression is as represented by (Expression 6).

Color difference:

$$d_{ij} = \sqrt{(x_{ij}-x_c)^2 + (y_{ij}-y_c)^2} \qquad \text{(Expression 6)}$$

Figure 12:
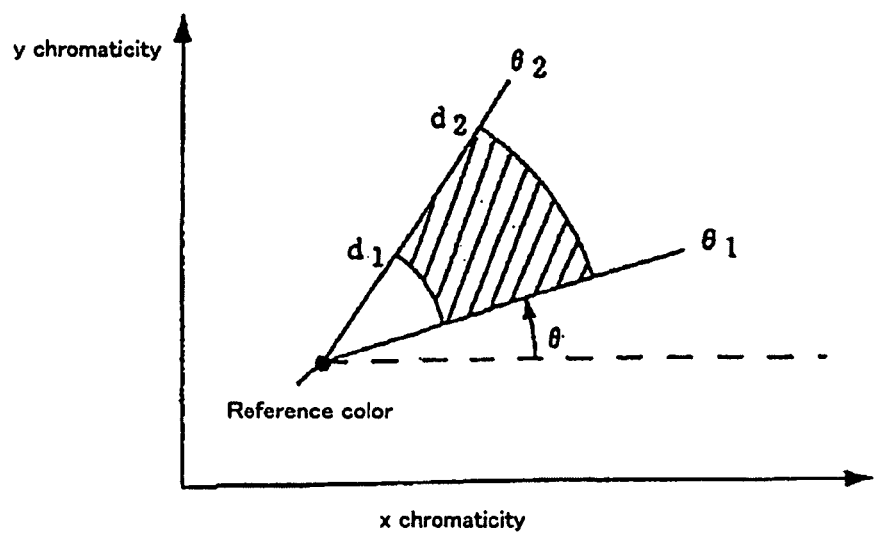
FIG. 12 is an xy chromaticity plane showing the method for obtaining a flaw candidate area.
Figure 13:
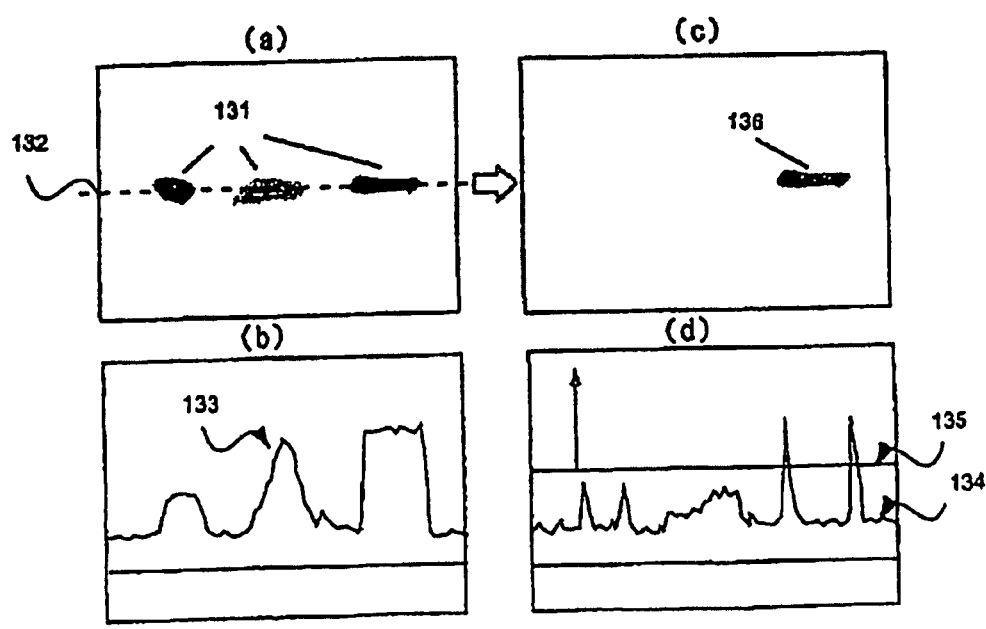
FIG. 13(a) is a diagram showing a flaw candidate area.
FIG. 13(b) is a diagram showing a color difference with respect to the reference white on 132 in FIG. 13(a)
FIG. 13(c) is a diagram showing a flaw area.
FIG. 13(d) is a diagram showing a color difference differentiation distribution.

As shown in FIG. 12, from the color hue and color difference in each position of the image with respect to the reference white, calculated as above, the range to be detected as a flaw is limited in the color hue (in FIG. 12, the color hue stands in the range $\theta_1 \le \theta \le \theta_2$), and the level of difference in vividness from the reference white is limited in the color difference (in FIG. 12, the color difference d stands in the range $d_1 \le d \le d_2$). Then a portion within the range is extracted as a flaw candidate area.

Among the flaw candidates obtained by limiting the range in the color hue and color difference in this manner, there is an area which is not to be detected as a flaw. For example, an area where the chromaticity gradually changes with respect to the reference white is not a flaw, but an area with a clear outline is a flaw. Accordingly, an area with smooth color change with respect to peripheral color is regarded as a normal portion or the pseudo flaw 3, and only an area with radical change is regarded as the flaw 2. At step 55, regarding a flaw candidate area, the change amount of color difference with respect to the reference white is obtained, and only an area where the change amount value is equal to or greater than a predetermined value is regarded as a flaw.

Referring to FIG. 13(a), a flaw candidate area 131 extracted at step 54 is shown. Numeral 133 in FIG. 13(b) denotes a graph of color difference with respect to the reference white on 132 in FIG. 13(a). Further, the change amount of the color difference 133 in each position on 132, i.e., differentiation of 133, is the color difference differentiation distribution 134 in FIG. 13(d). In this manner, in a position where the change amount of color difference with respect to the reference white is small, the differentiated value is small. As shown in FIG. 13(d), only an area where the differentiated value is greater than a constant value 135 is regarded as a flaw area. As a result, only a flaw area 136 as in FIG. 13(c) where the color difference is large, i.e., the outline is clear, is detected.

Figure 14:
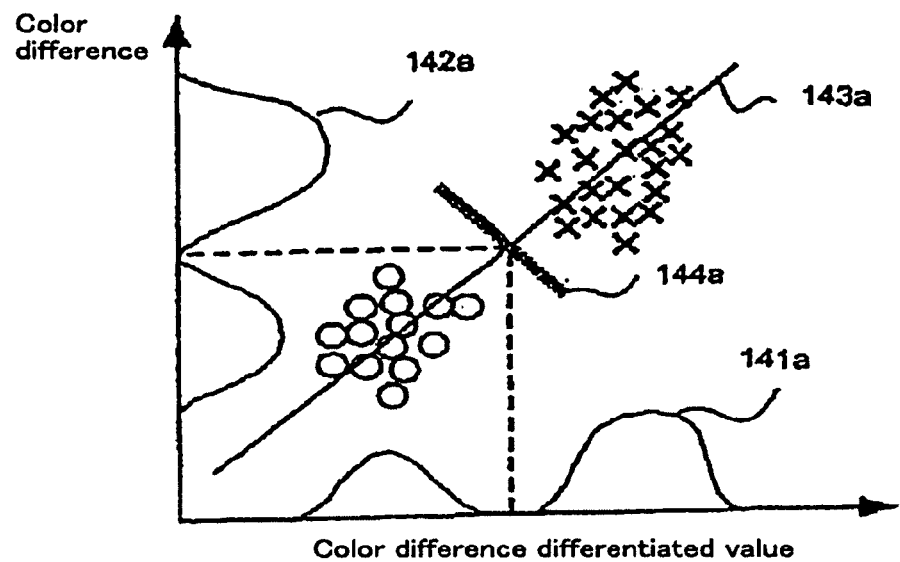
FIG. 14 (a) indicates a judgment line 144a in a color difference and color difference differentiation plane where a flaw and a pseudo flaw are apparently distinguishable, and FIG. 14 (b) indicates a judgment line 144b in a color difference and color difference differentiation plane where a flaw and a pseudo flaw are not separated.
Figure 14:
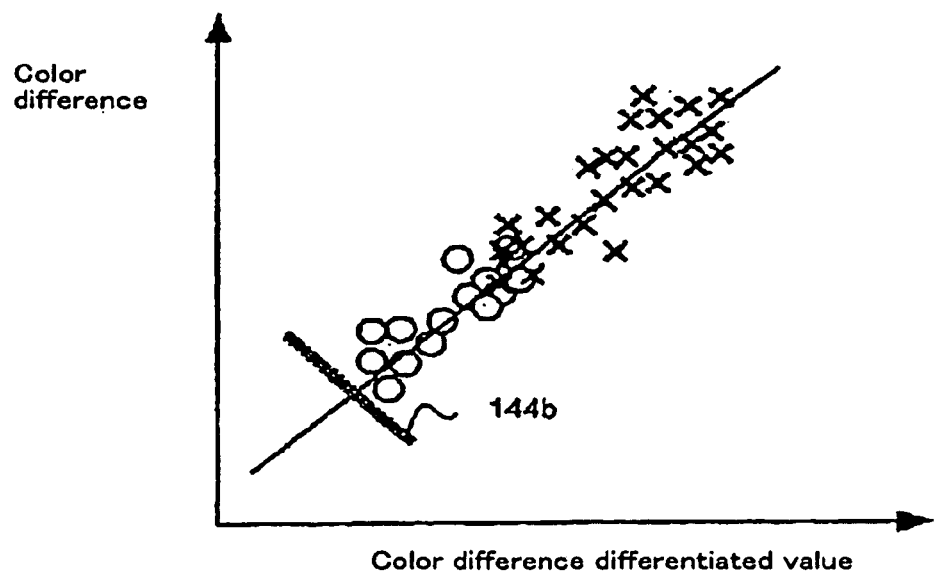

Next, the method for determination of the threshold value 135 will be described with reference to FIG. 14. In a graph of FIG. 14(a), the vertical axis is the maximum value of the color difference within each flaw candidate area extracted by the color hue and color difference, and the horizontal axis is the maximum value of the color difference differentiated value of the outline portion of each flaw area. The value of true flaw 2 is plotted by "X" and the value of the pseudo flaw 3, by "O". Further, 141*a* denotes a histogram of respective color difference differentiated values, and 142*a*, a histogram of color difference values. In a case where a flaw and a pseudo flaw are apparently distinguished from each other, a judgment line 144*a* is a straight line passing through the peak values of the histograms 141*a* and 142*a* and vertical to an inertial main axis 143*a* of the plotted points. Further, FIG. 14(*b*) illustrates a case where the flaw and the pseudo flaw are not separated, i.e., there is no peak or valley in the histogram. Here, the judgment line is 144*b*. That is, all the flaw candidate areas are detected as flaws, so as to prevent oversight.

Next, the method for flaw detection by magnetic particle testing will be described with reference to FIGS. 15 and 16.

Figure 15:
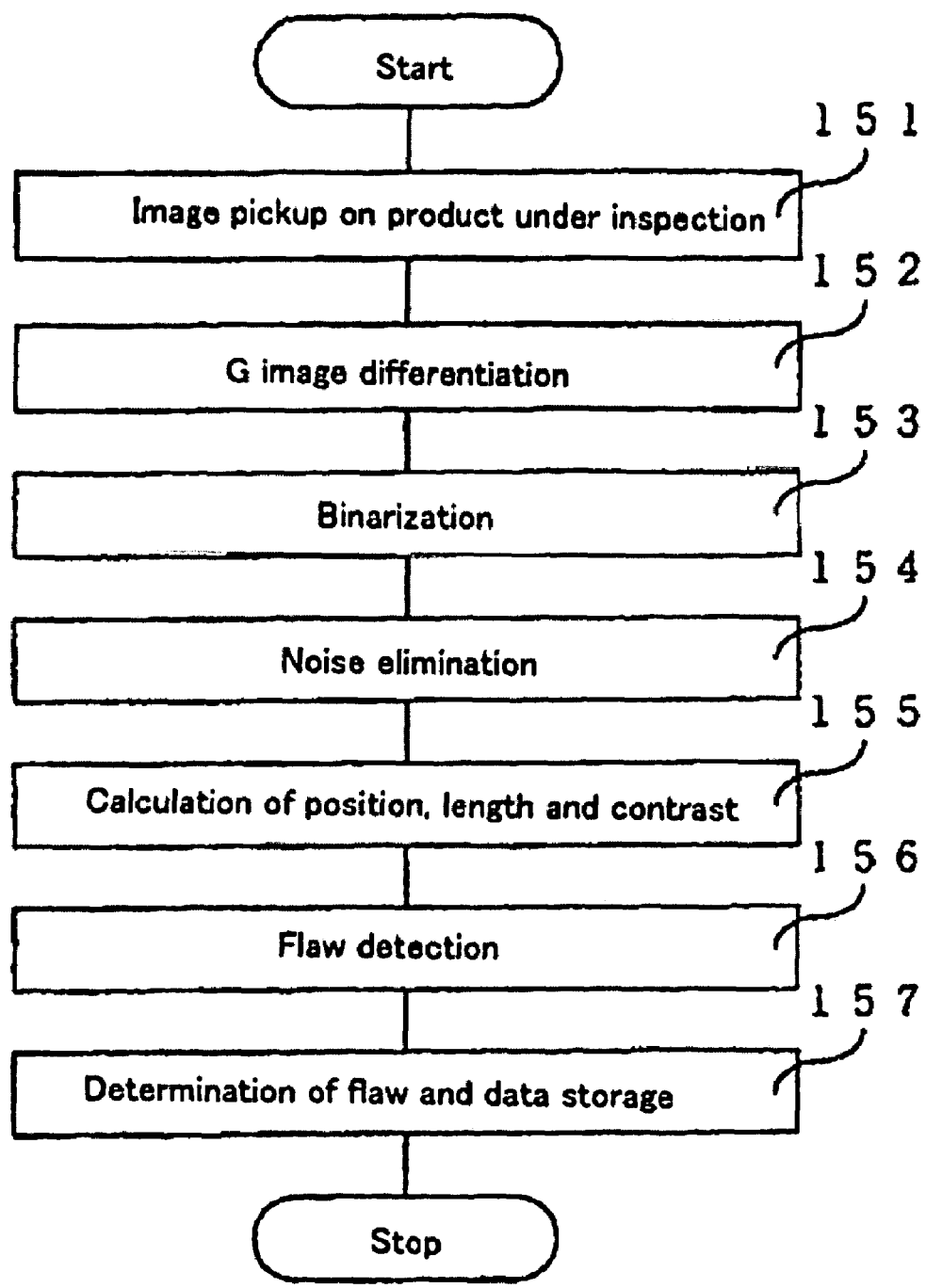
FIG. 15 is a flowchart showing an example of an image processing algorithm for magnetic particle testing according to an embodiment of the present invention.

FIG. 15 shows an example of an image processing algorithm to analyze the content of image memory 7 in magnetic particle testing. An RGB image is read 151. Next, differentiation processing is performed on a G image with the greatest amount of information on light emission from the fluorescent magnetic powder 152. By this processing, an area with a significant linear luminance change, such as a crack, is enhanced, while an area with high luminance but a small luminance change, such as accumulated magnetic powder, is not enhanced.

Next, a binarization threshold value is determined from an average value of the G differentiated image, and binarization is performed 153. From the binarized image, image noise such as an isolated point is eliminated 154, so that flaw candidates are obtained. Then, the length, contrast and the like of these flaw candidates are calculated 155. If these values are greater than predetermined values, the area is determined to be a flaw.

Figure 16:
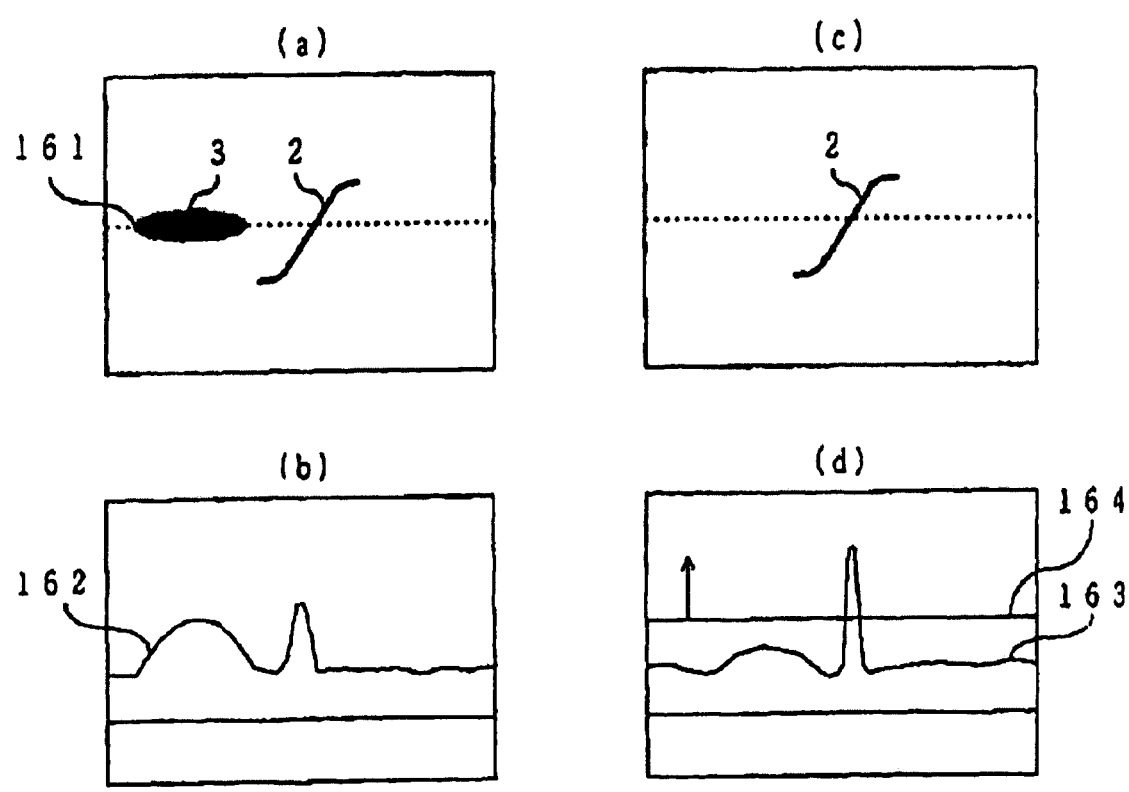
FIG. 16 (a) is an image of luminance distribution of a flaw and a pseudo flaw.

FIG. 16 shows the method for discrimination between a flaw and a pseudo flaw. For example, as shown in FIG. 16(*a*), if the luminance distribution of flaw 2 and pseudo flaw 3 is plotted on a line 161, luminance distribution 162 as in FIG. 16(*b*) is obtained. The luminance values of flaw 2 and pseudo flaw 3 are approximately equivalent to each other. If luminance distribution 162 is differentiated, luminance differentiated distribution 163 as shown in FIG. 16(*d*) is obtained. In flaw 2, the luminance radically changes, while in pseudo flaw 3, it smoothly changes. By judging the result of differentiation processing by using a judgment threshold value 164 as shown in FIG. 16(*d*), only flaw 2 can be extracted as in FIG. 16(*c*).

Figure 17:
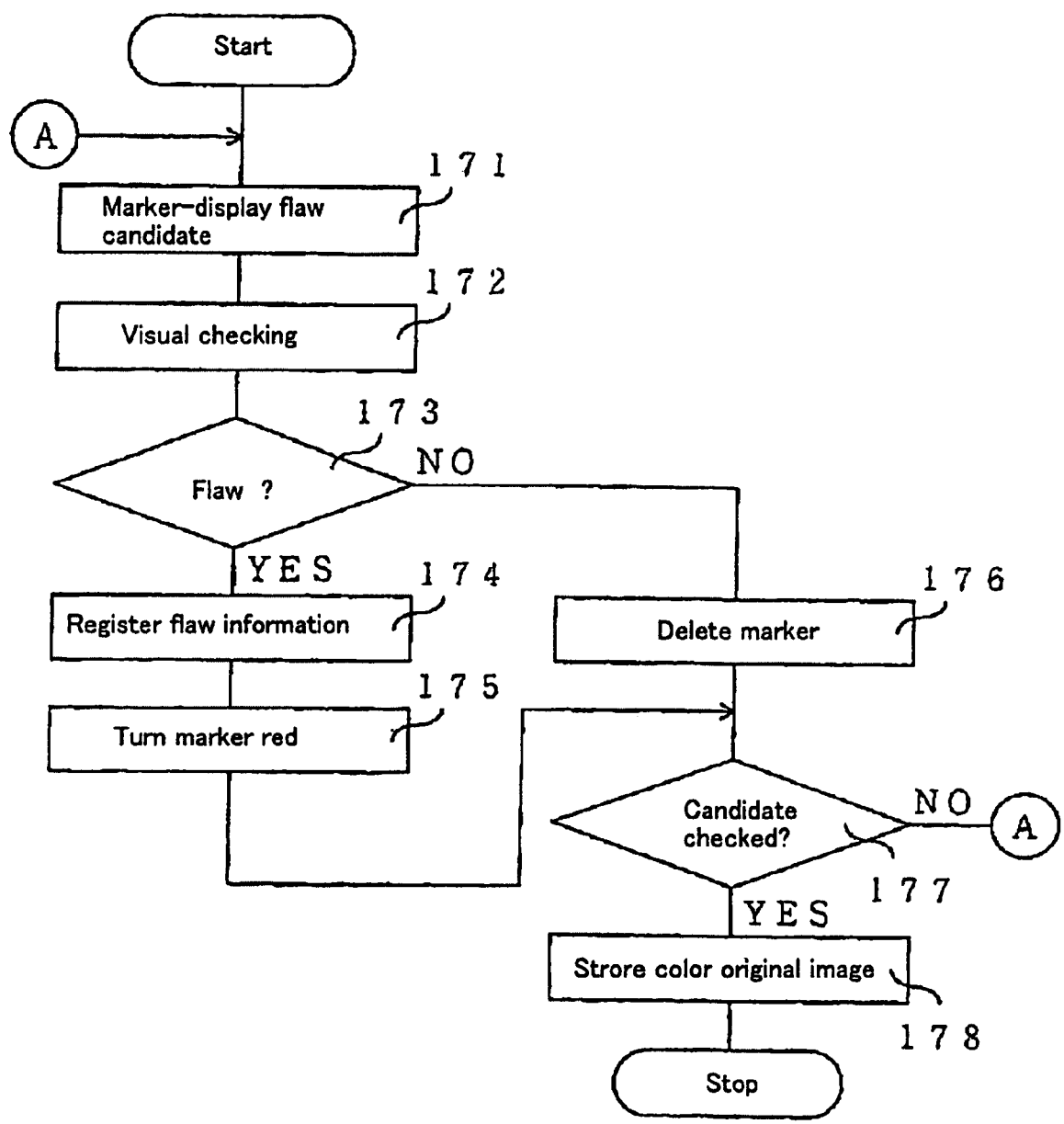
FIG. 17 is a flowchart showing the process of flaw verification and data storage in an embodiment of the present invention.

Referring to FIG. 17, flaw check and data storage will be described. The flaw and the pseudo flaw are separated by automatic inspection and only the flaw is extracted. However, to prevent oversight and misjudgment, in both liquid penetrant inspection and magnetic particle testing, a final flaw verification is performed by visual observation.

FIG. 17 is a flowchart showing the flaw verification process. First, a portion judged by automatic judgment as a flaw is marker-displayed as a flaw candidate 171. Next, computer 5 requires the inspector to judge the flaw candidates one by one 172. The inspector judges whether or not the candidate is a true flaw by viewing an original color image 173, and if the inspector judges that the candidate is a true flaw, the position, the length, the contrast and the like of the flaw are registered in data storage device 7 (174), and the marker is turned to red 175.

In flaw candidate verification, if the inspector judges a candidate as a pseudo flaw the marker is deleted 176. If another flaw candidate exists, the marker is displayed on the next flaw candidate. When all the flaw candidates have been checked 177, the original color image is stored in data storage device 7 (178).

Figure 18:
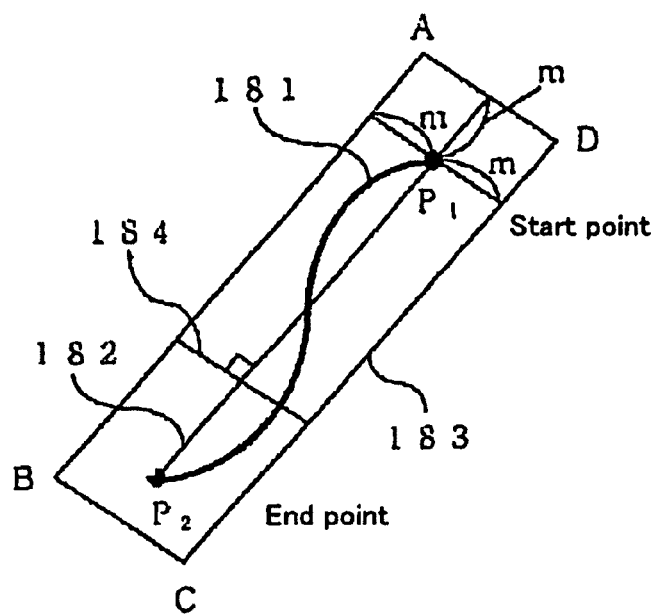
FIG. 18 is a diagram showing an example of the method for generating a flaw candidate marker in an embodiment of the present invention.

FIG. 18 shows an example of a method for flaw candidate marker generation. In a flaw candidate 181, a central line 182 connecting a start point P1 to an end point P2 is obtained, and longer sides AG and CD of a flaw candidate marker 183 are set in a position parallel to the central line and away from the line by a constant value m. Shorter sides AD and BC are similarly set. The length of flaw is the distance between the points P1 and P2. In magnetic particle testing, contrast related to the depth of the flaw is obtained by scanning a contrast calculation line 184 from P1 to P2, obtaining the difference between average luminance and maximum luminance on the line, obtaining the difference from P1 to P2, and obtaining an average value of the difference values as the contrast of the flaw. Note that the flaw candidate marker is not limited to a rectangular shape. The shorter sides AD and BC may be semicircular lines. It is important that the flaw is not hidden by the marker.

Figure 19:
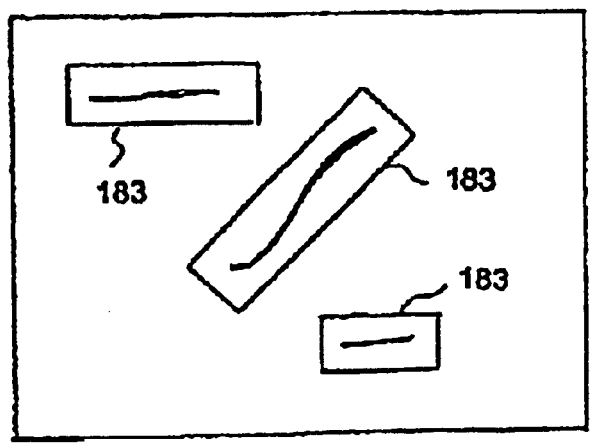
FIG. 19 is a diagram showing an example of a flaw candidate display method in an embodiment of the present invention.

FIG. 19 shows an example of a flaw candidate display method using a color monitor 9. Verification is performed sequentially from a long candidate, using the original image. At first, all the markers are displayed in white; then a marker of a candidate judged as a true flaw is turned to another color, e.g., red, and a marker of a candidate judged as a pseudo flaw is deleted.

Figure 20:
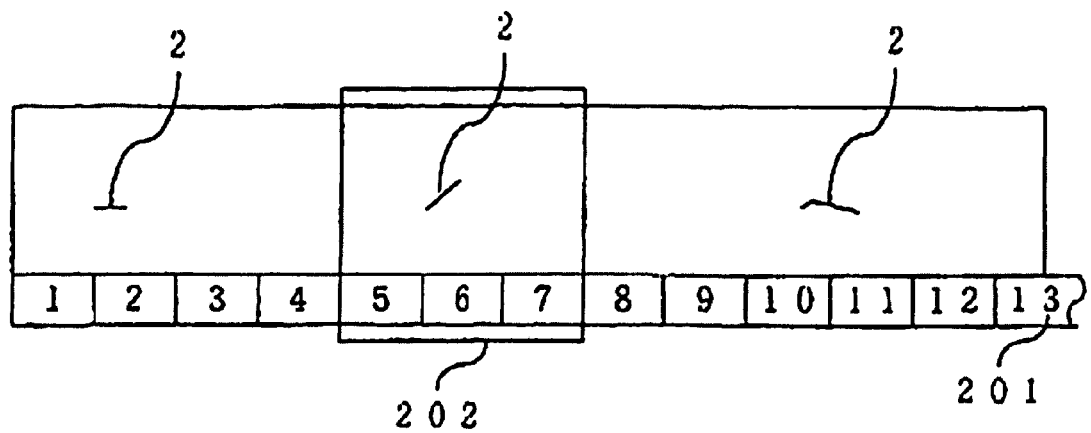
FIG. 20 is a diagram showing an example of the method for specifying an inspection position according to an embodiment of the present invention.

FIG. 20 shows an example of a method for specifying an inspection position when the object under inspection 1 is a long object. A scale 201 with markings is fixed to the object under inspection 1, so that the scale 201 enters in a camera view 202. The markings of the scale are, e.g., numerals at intervals of one centimeter. Further, scale 201 for liquid penetrant inspection and the scale for magnetic particle testing may be in different colors. For example, in liquid penetrant inspection, scale 201 is a white-based scale with red markings and numerals, but in magnetic particle testing, scale 201 is a white-based scale with markings and numerals in green fluorescent color.

Figure 21:
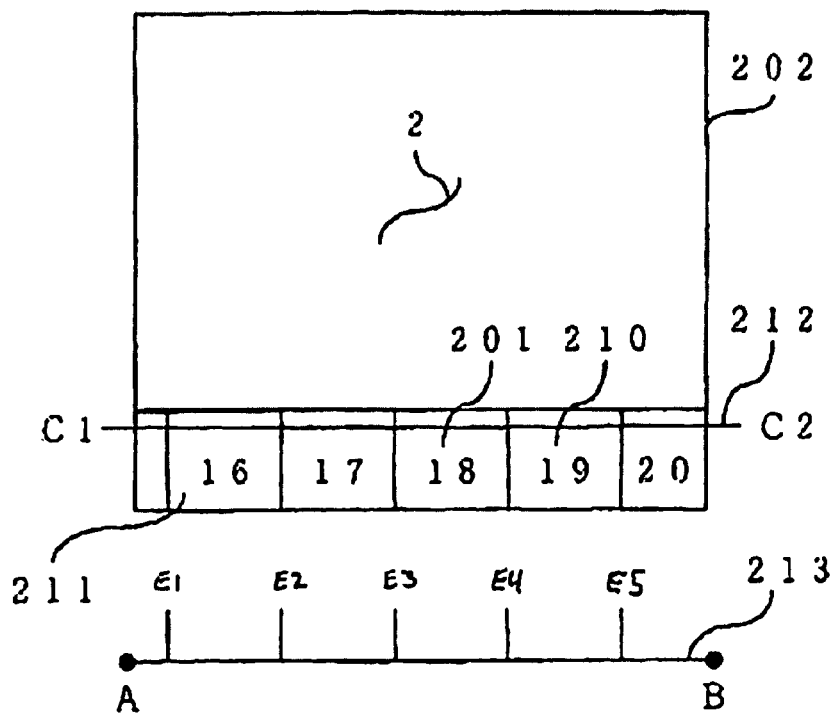
FIG. 21 is a diagram showing an example of an inspection image, including information specifying an inspection position according to an embodiment of the present invention.

FIG. 21 shows an example of an image obtained by image pickup. The image of scale 201 is simultaneously taken in a lower part of the image screen, and the camera position of object 1 is calculated from scale 201. That is, scale 201 has marking numerals 210 recognizable by the pattern matching method using the computer 5. Further, because scale 201 has tick lines 211 at intervals of, e.g., one centimeter, a more detailed camera position can be calculated. As an image signal of testing line 212 of C1 to C2 on the image, a cross section signal 213 is obtained. Then, positions of left end A and right end B, and E1, E2, E3, E4 and E5 of tick lines 211 are obtained. The image pickup magnification can be calculated from the positions of El, E2, E3, E4 and E5, and with marking numerals 210, and the accurate position of flaw 2 on the object 1 can be obtained.

Figure 22:
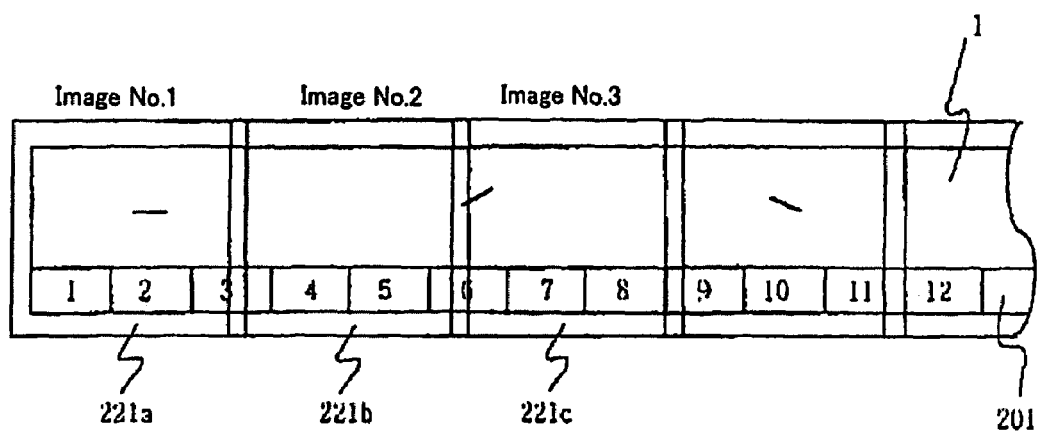
FIG. 22 is a diagram showing an example of the structure of inspection result data stored in the storage device 7.
Figure 22:
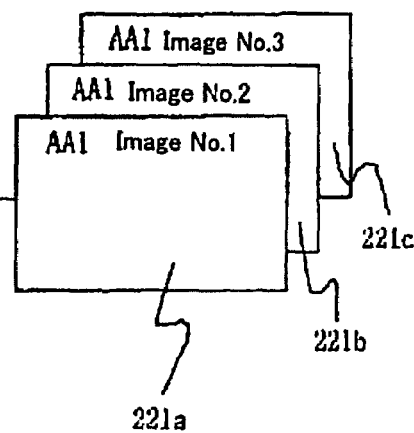

The inspection result is stored in storage device 7. FIGS. 22(*a*)–22(*c*) show an example storage format.

When a surface to be inspected of the object 1 is large and the entire inspection surface is larger than one inspection image screen, the surface is divided into several images and image pickup and inspection are performed on the images. The image pickup ranges overlap with each other by a small amount on the inspection surface. Numerals 221*a*, 221*b* and 221*c* denote divided images of object 1. The inspection is performed on the respective divided images. As denoted by 222, the result is that complete information for the entire image of each object under inspection is stored, and further, information on the position, the length, the area, the chromaticity, the color hue, and the like of each flaw are stored with the image information.

The inspector first displays the data 222 of each inspected object stored in storage device 7 on the display screen of monitor 6 and checks it. Further, if the inspector wants to see a portion of a flaw in detail, a corresponding divided image is read from the name of the object under inspection and its image number, and is displayed on the screen of monitor 6. At this time, the information on the position, the length, the area, the chromaticity and color hue, stored in correspondence with the displayed image data, can also be displayed on the screen of monitor 6.

Further, as detected flaw candidates are displayed with enhancement using a marker or the like on the display screen, oversight of a flaw which is larger than a size of about 0.1 to 0.3 mm, about the same size as that in conventional visual observation inspection, can be prevented.

Moreover, by increasing the image detection magnification, a flaw finer than a visually observable size can be detected. Further, by enlarging and displaying the flaw finer than a visually observable size on the display screen, the position, the length, the area, the chromaticity, the color hue and the like of the flaw can be checked on the display screen.

According to the present invention, image input is performed by using a color video camera, and in flaw inspection by magnetic particle testing, ultraviolet light reflected from an object under inspection can be reduced by the ultraviolet light reduction filter. Accordingly, the inspector can easily check the results of automatic flaw inspection. Moreover, because the flaw candidates are automatically indicated on the display screen, oversight in inspection can be almost fully prevented. Further, because the inspection image is stored, after the inspection, the stored image can be displayed on the display screen and the flaw can be checked again. Thus, the reliability of inspection is improved.

Further, according to the present invention, because a the color video camera is used, the automatic flaw inspection by magnetic particle testing and liquid penetrant inspection can be performed by the same sensor probe. Thus, the convenience is greatly improved.

The invention may be embodied in other specific forms without departing from the spirit or essential characteristics thereof. The present embodiment is, therefore, to be considered in all respects as illustrative and not restrictive, the scope of the invention being indicated by the appended claims rather than by the foregoing description, and all changes that come within the meaning and range of equivalency of the claims are therefore intended to be embraced therein.

The preceding has been a description of the preferred embodiment of the invention. It will be appreciated that deviations and modifications can be made without departing from the scope of the invention, which is defined by the appended claims.

What is claimed is:

1. A method of liquid penetrant testing, comprising the steps of:
    illuminating a surface of a sample to be inspected with polarized light;
    picking up an image of the surface illuminated with the polarized light by a color camera;
    processing said image picked up in the obtaining step;
    storing an image processed in the processing step in a memory; and
    displaying said image stored in said memory,
    wherein, in the step of obtaining, said image of said surface is picked up by said color camera over plural visual field,
    wherein, in the step of processing, said image is processed by calibrating said image by using a parameter which is calculated from data of an image of a color chart for calibration which contains white, red and plural colors between white and red picked up by said color camera.

2. The method according to claim 1, wherein, in the step of processing, a chromaticity of the obtained image is converted by using said parameter.

3. The method according to claim 1, wherein the image displayed in the displaying step is associated with a positional information.

4. The method according to claim 1, wherein the positional information is obtained with the image in the obtaining step.

5. The method according to claim 1, wherein, in the step of processing, said image is processed to extract a flaw candidate, and in the step of storing, an image of said extracted flow candidate is stored in said memory.

6. An apparatus for liquid penetrant testing, comprising:
    an illuminator which illuminates a surface of a sample to be inspected with polarized light;
    an image pick up unit which pick up an image of the surface illuminated with the polarized light by a color camera;
    a processor which processes an image picked up by said image pick up unit;
    a memory means for storing an image processed by said processor; and
    a display unit which displays said image stored in said memory,
    wherein said image pick up unit picks up said image of said surface by said color camera over plural visual field,
    wherein, said processor processes said image by calibrating said image using a parameter which is calculated from data of an image of a color chart for calibration which contains white, red and plural colors between white and red picked up by said image pick up unit.

7. The apparatus according to claim 6, wherein said processor converts a chromaticity of the obtained image by using said parameter.

8. The apparatus according to claim 6, wherein said display unit displays said image associating with a positional information.

9. The apparatus according to claim 8, wherein said positional information is obtained by said image pick up unit with the image.

10. The apparatus according to claim 6, wherein said processor processes said image to extract a flaw candidate, and said memory means stores an image of said extracted flow candidate.

* * * * *